United States Patent
Alimi et al.

(10) Patent No.: US 7,683,636 B2
(45) Date of Patent: Mar. 23, 2010

(54) STRUCTURE FOR CAPACITIVE BALANCING OF INTEGRATED RELATIVE HUMIDITY SENSOR

(75) Inventors: Yousef M. Alimi, Allen, TX (US); Richard A. Davis, Plano, TX (US)

(73) Assignee: Honeywell International Inc., Morristown, NJ (US)

( * ) Notice: Subject to any disclaimer, the term of this patent is extended or adjusted under 35 U.S.C. 154(b) by 159 days.

(21) Appl. No.: 11/977,799

(22) Filed: Oct. 26, 2007

(65) Prior Publication Data

US 2009/0108852 A1 Apr. 30, 2009

(51) Int. Cl.
G01R 27/26 (2006.01)
H01G 5/012 (2006.01)

(52) U.S. Cl. .................. 324/664; 324/689; 361/286

(58) Field of Classification Search .............. 324/664, 324/689; 361/286
See application file for complete search history.

(56) References Cited

U.S. PATENT DOCUMENTS

| | | | |
|---|---|---|---|
| 4,057,823 A | 11/1977 | Burkhardt et al. | |
| 4,470,096 A | 9/1984 | Guertin | |
| 6,614,241 B2 * | 9/2003 | Schmitt et al. | 324/664 |
| 6,647,782 B2 * | 11/2003 | Toyoda | 73/335.04 |
| 6,724,612 B2 | 4/2004 | Davis et al. | 361/328 |
| 6,867,602 B2 | 3/2005 | Davis et al. | 324/664 |
| 2004/0008471 A1 * | 1/2004 | Davis et al. | 361/306.3 |
| 2004/0177685 A1 | 9/2004 | Yokura et al. | |

FOREIGN PATENT DOCUMENTS

JP 2003-004683 A 1/2003

* cited by examiner

*Primary Examiner*—Amy He
(74) *Attorney, Agent, or Firm*—Kermit D. Lopez; Luis M. Ortiz

(57) ABSTRACT

An improved relative humidity sensor apparatus that provides a more accurate measurement of humidity in the presence of water condensation. A series capacitive sensor includes a thin porous platinum top plate, a humidity sensitive polyimide dielectric, and two metal bottom plates on a semiconductor substrate. The two capacitors can be wired in series such that the metal bottom plates form independent, electrically driven connections. The thin top layer can form a top plate. Changes in humidity affect the humidity sensitive dielectric thereby causing changes in the capacitive value. A P-well layer and a P-plus layer can be added at the perimeter of the substrate to create a path for a parasitic capacitance caused by water condensation to connect to one or more connection nodes, thereby preventing erroneous measurements of humidity in the presence of water condensation.

20 Claims, 3 Drawing Sheets

STRUCTURE FOR CAPACITIVE BALANCING OF INTEGRATED RELATIVE HUMIDITY SENSOR

TECHNICAL FIELD

Embodiments are related to semiconductor wafer-based devices. Embodiments are also related to relative humidity sensors. Embodiments are additionally related to relative humidity sensor structures for the accurate measurement of humidity.

BACKGROUND OF THE INVENTION

Humidity plays a very major role in various industrial and commercial applications. Monitoring and controlling humidity is of great importance for the reliable operation of various systems. For example, solid-state semiconductor devices are found in most electronic components today. Semiconductor-based sensors are fabricated using semiconductor processes. Humidity sensors represent but one class of semiconductor-based sensors finding a useful industrial application. Modern manufacturing processes, for example, generally require measurement of moisture contents corresponding to dew points between −40° C. and 180° C., or a relative humidity between 1% and 100%. There is also a need for a durable, compact, efficient moisture detector that can be used effectively in these processes to measure very small moisture content in gaseous atmospheres.

Humidity can be measured by a number of techniques. In a semiconductor-based system, for example, humidity can be measured based upon the reversible water absorption characteristics of polymeric materials. The absorption of water into a sensor structure causes a number of physical changes in the active polymer. These physical changes can be transduced into electrical signals which are related to the water concentration in the polymer and which in turn are related to the relative humidity in the air surrounding the polymer. Two of the most common physical changes are variations in resistance and the change in dielectric constant, which can be respectively translated into a resistance change and a capacitance change. It has been found, however, that elements utilized as resistive components suffer from the disadvantage that there is an inherent dissipation effect caused by the dissipation of heat due to the current flow in the elements necessary to make a resistance measurement. The result includes erroneous readings, among other problems.

Elements constructed to approximate a pure capacitance avoid the disadvantages of the resistive elements. It is important in the construction of capacitive elements, however, to avoid problems that can arise with certain constructions for such elements. In addition, there can also be inaccuracy incurred at high relative humidity values where high water content causes problems due to excessive stress and the resulting mechanical shifts in the components of the element. By making the component parts of the element thin, it has been found that the above-mentioned problems can be avoided and the capacitance type element can provide a fast, precise measurement of the relative humidity content over an extreme range of humidity as well as over an extreme range of temperature and pressure and other environmental variables.

A conventional capacitive humidity sensor, in general, can include a semiconductor substrate, and a pair of electrodes, which are formed on a surface of the semiconductor substrate and face each other across a particular distance. A humidity-sensitive film may also be placed between the electrodes and formed on a surface of the semiconductor substrate. The capacitance of the film changes in response to humidity. The sensor detects humidity by detecting changes in capacitance between the pair of electrodes in response to variations in the surrounding humidity. The capacitance of the film changes in response to humidity, and the sensor detects humidity by detecting changes in capacitance between the electrodes with respect to changes in the surrounding humidity.

Humidity sensing elements of the capacitance sensing type usually include a moisture-insensitive, non-conducting structure with appropriate electrode elements mounted or deposited on the structure, along with a layer or coating of a dielectric, highly moisture-sensitive material overlaying the electrodes and positioned so as to be capable of absorbing water from the surrounding atmosphere and attaining equilibrium in a short period of time. Capacitive humidity sensors are typically made by depositing several layers of material on a substrate material.

Referring to FIG. 1, a perspective view of the basic components of a prior art semiconductor-based humidity sensor 100 are illustrated. A semiconductor humidity sensor 100 is generally fabricated on a silicon substrate 110. The active sensor components include respective lower and upper electrically conductive plates 120, 140 sandwiching a humidity sensing medium 130, such as a polymer. The polymer material is sensitive to humidity, and its electrically conductive properties (e.g., resistance and/or capacitance) change as it absorbs moisture, or as it dries. The lower and upper plates 120, 140 can be electrically connected to sensor circuitry (i.e., not shown in FIG. 1). A protective layer 150 can be used to protect the active components of the sensor (e.g., top plate 140 and sensing medium 130) from debris 160. Upper plate 140 can be designed to be porous in order to enable humidity to enter into the sensing medium from an external environment of interest 170 (i.e., the monitored environment of interest).

Referring to FIG. 2, a cut-away side view of a prior art relative humidity sensor 200 is illustrated. The example humidity sensor 200 depicted in FIG. 2 includes a substrate 210. Insulating materials 220 can function as a buffer between the substrate 210 and respective first and second lower capacitor plates 240, 245. First lower capacitor plate 240 is electrically connected to a first connector 230. Second lower capacitor plate 245 is electrically connected to a second connector 235. A sensing medium 260 is generally disposed on top of the first and second lower capacitor plates 240, 245. A porous platinum top capacitor plate 250 is then disposed on top of the sensing medium 260. A protective layer 255 can also be disposed above the top plate 250 for protection of the top plate 250 and sensing medium layer 260. Two capacitors Cx1 and Cx2 are schematically illustrated in respective positions within the sensing medium 260 between the first lower capacitor plate 240 and top capacitor plate 250 and the second lower capacitor plate 245 and the top capacitor plate 250. The gap/barrier 265 can be between the first and second lower contact plates 240, 245, to create the series capacitor configuration for Cx1 and Cx2.

As depicted in the prior art illustration of FIG. 2, capacitor Cx1 can include a common top plate 250 (common to both Cx1 and Cx2) and a first lower capacitor plate 240 in further electrical contact with a first electrical contact 270. Capacitor Cx2 generally includes common top plate 250 as its first contact and a second lower capacitor plate 245, which is in further electrical contact with second electrical contact 275. Also illustrated is a parasitic capacitor Cct which can be located between the upper plate 250 and the silicon substrate 210. The total capacitance between the pair of electrodes in response to changes in the surrounding humidity can be expressed in the form of equation (1) as follows:

$$C_{Total} = (CX1*CX2)/(CX1+CX2+Cct) \quad (1)$$

Condensation occurs whenever the surface temperature of the sensor's active area drops below the ambient dew point of the surrounding gas. The condensation of water can be formed on the sensor or any surface even if the surface temperature momentarily drops below the ambient dew point. Small temperature fluctuations near the sensor can unknowingly cause condensation to form when operating at humidity levels above 95%. Because of this, a sensor's recovery period from either condensation or wetting is much longer than its normal time response.

The problem associated with prior art capacitive humidity sensors such as, for example, sensor 200, is that the condensation of liquid water on the sensor creates a capacitive path 225 having parasitic capacitance CW with respect to the substrate 210 as depicted in FIG. 2. This effect causes the total capacitance value $C_{Total}$ to decrease, and therefore generates an erroneous low humidity value. In the event of water condensation, the total capacitance value can be expressed as indicated in equation (2) below:

$$C_{Total} = (CX1*CX2)/(CX1+CX2+Cct+CW) \quad (2)$$

As shown in equation (2), the total capacitance value $C_{Total}$ decreases due to the presence of water condensation, which results in an inaccurate measurement of humidity.

Various packaging techniques exist which are designed to prevent condensation on the sensing surface. These can be useful, but limitations in cost and packaging do not always allow for these solutions. Hence, another solution is needed that avoids the deleterious effects of condensation without modifications to the packaging. The current invention accomplishes this by embedding the solution in the circuit without adding cost. This is accomplished by modifying the circuit so that the parasitic capacitance created by water condensation is redirected to a different part of the circuit.

Based on the foregoing it is believed that a need exists for an improved relative humidity sensor that redirects the path of parasitic capacitance due to condensation to provide a more accurate measurement of humidity.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for improved sensor methods and systems.

It is another aspect of the present invention to provide for an improved structure for capacitive balancing of relative humidity sensors in the presence of water and/or moisture condensation.

The aforementioned aspects and other objectives and advantages can now be achieved as described herein. An improved relative humidity sensor for more accurate measurement of humidity in the presence of water condensation is disclosed. The relative humidity sensor generally includes a pair of electrodes with a gap-interposed therebetween to form series sensing capacitors on a silicon substrate with a silicon oxide film configured on a surface. A moisture-sensitive structure can be provided so as to cover the pair of capacitor plates with a silicon nitride film interposed therebetween. A P-well and a P-plus layer can be added to the perimeter of the substrate to create a path for a parasitic capacitance caused by water condensation to connect to one node of the sensing capacitor. Because the P-well and P-plus layers are already included in the normal fabrication procedure, there is no additional cost incurred to include these layers around the perimeter of the sensor die.

The capacitance formed between the two electrodes changes in accordance with ambient humidity. The humidity sensing capacitor structure design disclosed herein can therefore increase the total capacitance value in the presence of water condensation on the sensing element and thereby give a more accurate measurement of humidity. The structure and the P-well and P-plus layers can be fabricated utilizing standard silicon wafer processing techniques commonly used on existing relative humidity sensors. The improved structure proposed in this invention is accomplished utilizing only photo-mask changes in the wafer fabrication process flow so that no additional processing cost is incurred.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
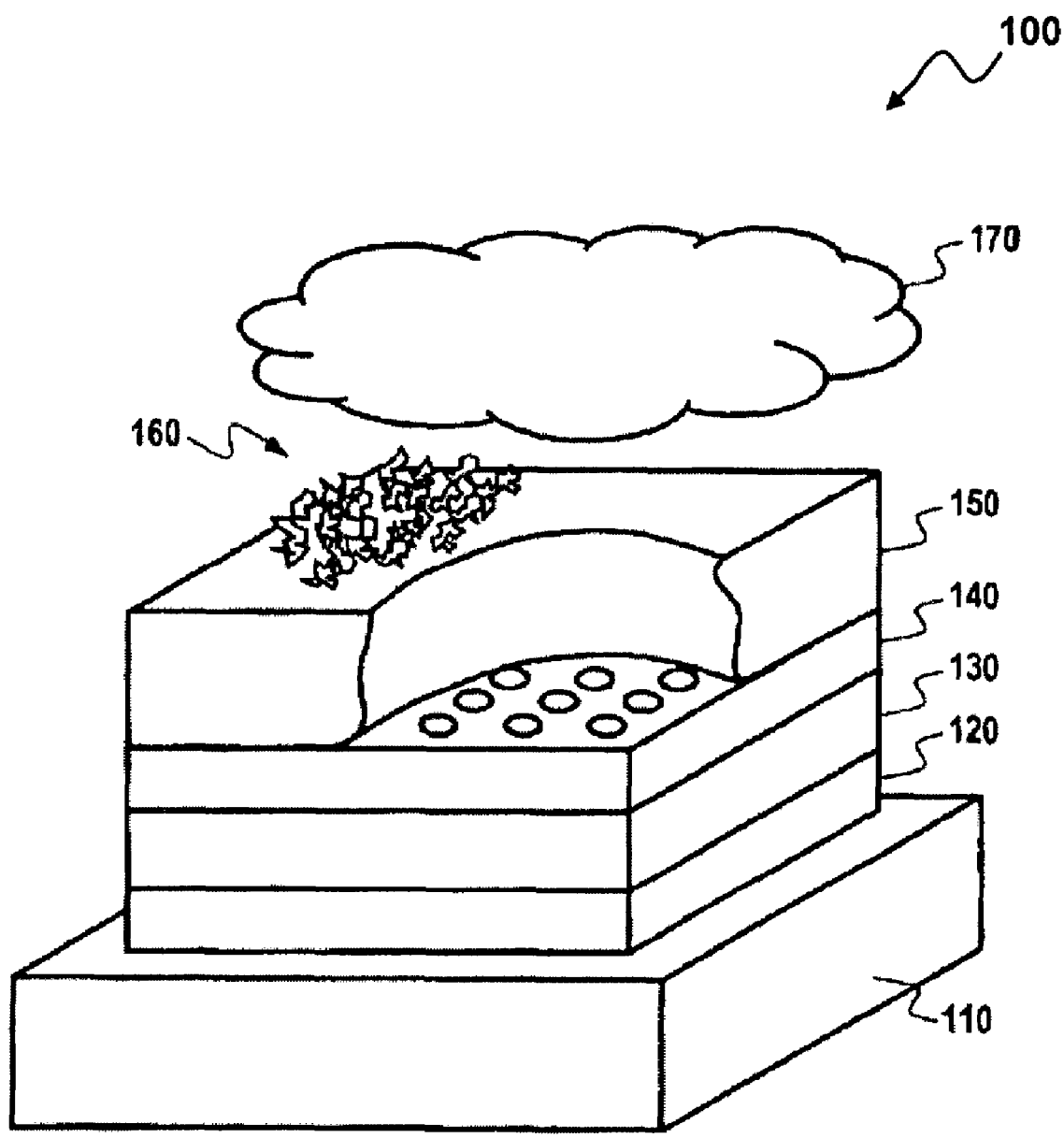
FIG. 1 illustrates a prior art humidity sensor.
Figure 2:
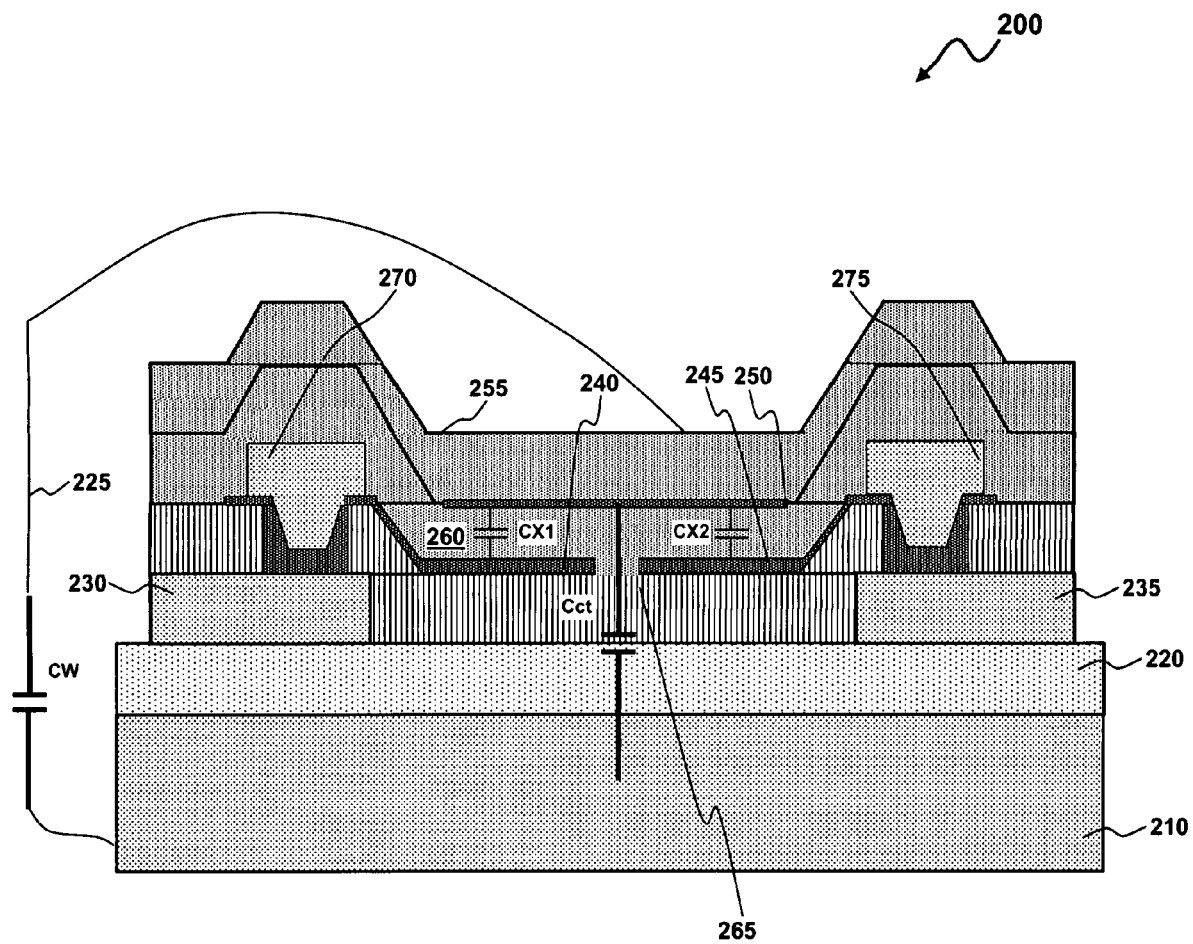
FIG. 2 illustrates a cut-away side view of a prior art humidity sensor.
Figure 3:
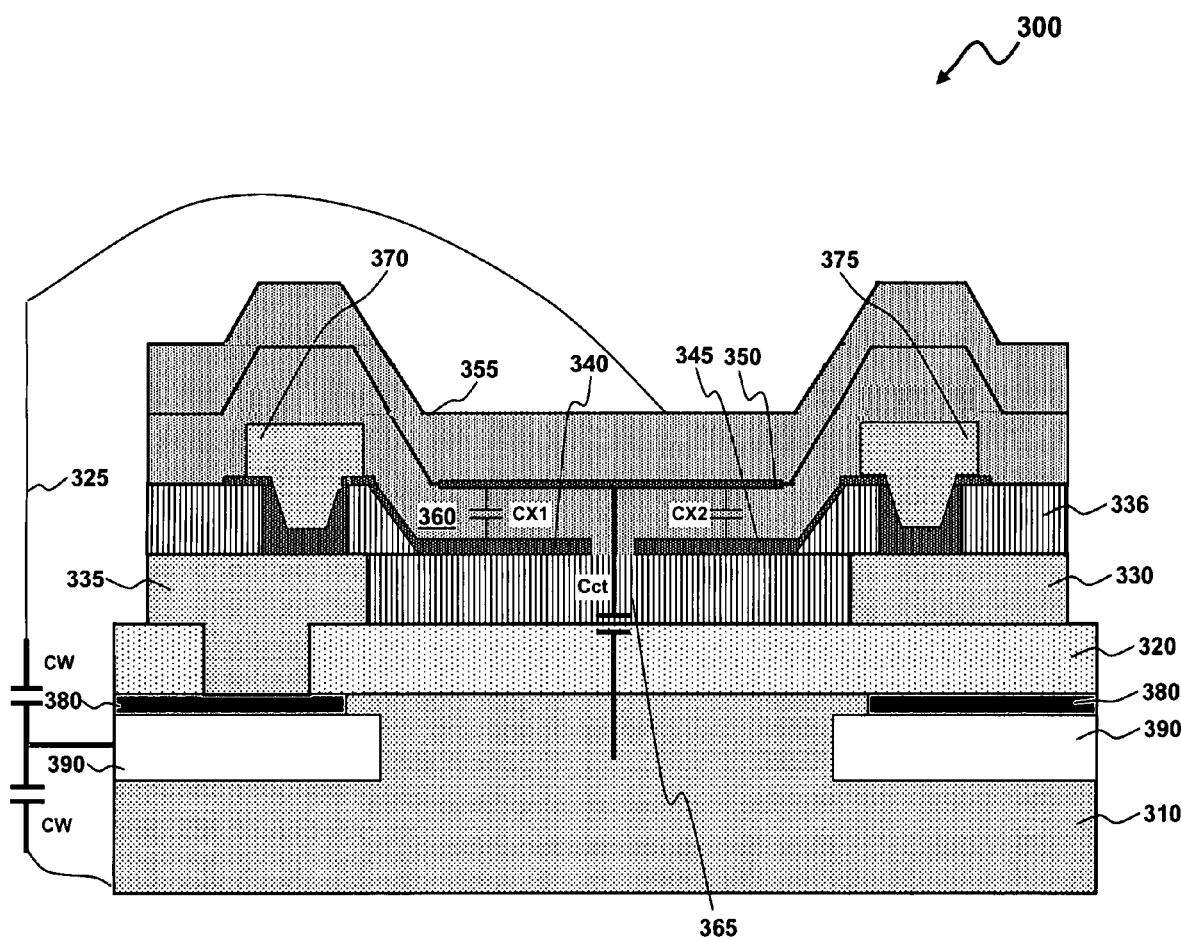
FIG. 3 illustrates a cut-away side view of an improved relative humidity sensor apparatus, in accordance with a preferred embodiment.

Referring to FIG. 3, a cut-away side view of an improved relative humidity sensor apparatus 300 is illustrated, in accordance with a preferred embodiment. It should be understood that there are other integrated components of the sensor that are not depicted in the figure. The humidity sensor apparatus 300 depicted in FIG. 3 can be used for humidity control in an air conditioner or to detect humidity for weather observation purposes. It is understood, however, that a wide variety of other applications for humidity sensor apparatus 300 can also be implemented, depending upon design goals and considerations. As depicted in FIG. 3, an N-type silicon substrate 310 can be employed as a semiconductor substrate 310. A silicon oxide film 320 can be formed on the semiconductor substrate 310 as a first insulation film. First and second electrodes 330 and 335 are configured on an identical plane of the silicon oxide film 320 so as to oppose each other with a gap 365 interposed between them.

A material capable of being utilized in a normal semiconductor fabrication facility can be employed to form the first and second electrodes 330 and 335. Such material can be, for example, Al, Ti, Au, Cu, poly-Si, and the like. In one particular embodiment, a silicon nitride film 336 can be formed on first insulation film 320 and around the electrodes 330 and 335 as a second insulation film. It can be appreciated, however, that in other embodiments, materials other than silicon nitride may be utilized to implement film 336. The silicon nitride film 336 can be formed by plasma CVD method or the like, so as to have the same thickness over the whole area on the semiconductor substrate 310.

As shown in FIG. 3, the pair of electrodes 330 and 335 can be equipped with a first electrical contact 370 and a second electrical contact 375 through which the electrodes 330 and 335 are connected to a signal processing circuit (not shown in FIG. 3) for detecting the variation of the sensing capacitance between the pair of electrodes 330 and 335, respectively. Furthermore, according to such an embodiment, the capacitance type humidity sensor apparatus 300 can be formed on the semiconductor substrate 310, and thus the signal processing circuit for detecting the variation of the capacitance type humidity sensor apparatus 300 can be formed on the principal surface of the semiconductor substrate 310.

A sensing medium 360 having a permittivity that changes according to humidity can be formed on capacitor plates 340, 345, and silicon nitride layer 336. Porous platinum top plate 350 through which water is allowed to permeate can be formed so as to cover the humidity sensing medium 360. When water infiltrates into the humidity sensing medium 360, the dielectric constant of the humidity sensing medium 360 is varied in accordance with the amount of water.

As a result, the series sensing capacitors as indicated by CX1 and CX2 are constructed by the pair of plates 340, 345, and the top porous plate 350 with the humidity sensing medium 360 as a part of the dielectric material. Humidity can be detected on the basis of the sensing capacitance between the pair of electrodes 330 and 335, because the amount of water contained in the humidity sensing medium 360 corresponds to the ambient humidity around the capacitance type humidity sensor apparatus 300.

As described above, the variation of the capacitance between the pair of electrodes 330 and 335 in accordance with the humidity variation of the humidity sensing medium 360 can be increased with increasing relative humidity.

A P-well layer 390 (i.e., an example of a second semiconductor substrate) can be formed on the surface of the silicon semiconductor substrate 310. A P-plus layer 380 can be diffused above the P-well layer. The P-well layer 390 and P-plus layer 380 can be fabricated by implanting appropriate dopants below the buried oxide layer 320. The layers can also be fabricated utilizing standard silicon wafer processing techniques commonly used in silicon wafer fabrication.

The P-well layer 390 and the P-plus layer 380 create a path 325 for the parasitic capacitance CW caused by water condensation to connect to one node of the sensing capacitor CX1 (i.e., the sensing capacitor CX1 of the sensing medium 360). The relative humidity sensing capacitor CX1 and CX2 can be fabricated utilizing standard silicon wafer processing techniques commonly used to configure existing relative humidity sensors. Formation of the P-well layer 390 and the P-plus layer 380 can be accomplished by taking advantage of photomask changes in the wafer fabrication process flow.

A hygroscopic macro molecule organic material can be employed as the moisture sensing medium 360. Specifically, a polyimide or butyric acetyl cellulose or the like can be employed. In such an embodiment, the sensing medium 360 can be composed of a polyimide. When molecular water is absorbed in the film 360, the permittivity of the film 360 changes according to the amount of absorbed water molecules, since water molecules have a high permittivity, which thereby causes a change in capacitance between the detection electrodes 330 and 335. An area where the moisture-sensitive film 360 is located on the semiconductor substrate 310 constitutes a humidity-sensing portion 360. Namely, ambient humidity can be detected via the humidity-sensing portion 360 based on the capacitance formed between the detection electrodes 330 and 335.

The total capacitance between the pair of electrodes 330 and 335 in response to changes in the surrounding humidity can be expressed in the form of equation (3) as follows:

$$C_{Total} = (CX1 * CX2)/(CX1 + CX2 + Cct) \quad (3)$$

The total capacitance value due to the presence of water condensation is given by equation (4):

$$C_{Total} = ((CX1 + CW) * CX2)/((CX1 + CW) + CX2 + Cct)) \quad (4)$$

As demonstrated by equation (4), the total capacitance value $C_{Total}$ in presence of water condensation on the sensor increases since the parasitic capacitance CW path is re-directed to the sensing capacitor CX1, which provides a more accurate measurement of humidity.

In general, the methodology for forming the sensor apparatus 300 can be implemented as follows. A semiconductor substrate and a first insulator layer can be formed on the semiconductor substrate in association with a second insulator layer formed on the first insulator layer. A P-plus layer and a P-well can be then be formed on a perimeter of the semiconductor substrate wherein the P-plus layer and the P-well layer create a path for a parasitic capacitance caused by water condensation to connect to at least one node of a sensing capacitor. As indicated in FIG. 3, the pair of contacts 370 and 375 are associated with only one pair of capacitor plates 340 and 345 formed on the second insulator layer 336, wherein the pair of capacitor plates are isolated from one another with a space 365 formed therein. That is, in some embodiments, there may be only one pair of capacitor plates, as opposed to a pair of capacitor plates formed on the first insulator layer and another pair of capacitor plates formed on the second insulator layer.

A humidity sensitive dielectric layer can be formed on the second insulator layer and the pair of capacitor plates, wherein a relative permittivity of the humidity sensitive layer varies in accordance with a humidity such that a pair of series capacitance additionally varies in accordance with the humidity to thereby provide an increased accurate measurement of the humidity. Additionally, a porous electrically conductive plate can be configured on the humidity sensitive dielectric layer, wherein the porous electrically conductive plate includes a common top plate with respect to the pair of capacitive plates. A protective layer can be formed on the porous electrically conductive plate, wherein the protective layer protects the common top plate and the humidity sensitive layer. The first insulator layer can constitute silicon oxide and the second insulator layer can be silicon nitride. The P-plus layer and the P-well layer can be fabricated utilizing a standard silicon wafer processing technique.

The disclosed device can be utilized to sense the relative humidity in the ambient environment around the sensor. During operation, a relative humidity level can be sensed and then the sensor generates a voltage output proportional to the relative humidity. This voltage can then be used by other circuits to implement functions such as, for example, relative humidity control, enthalpy control for building HVAC, weather sensing instruments, process controls for drying, process controls for batch or any continuous production where relative humidity is a parameter that controls the output of a process or is related to some process variable to be controlled, length or end of cycle in drying applications, and other applications.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An improved relative humidity sensor apparatus, comprising:
   a semiconductor substrate and a first insulator layer formed on said semiconductor substrate in association with a second insulator layer formed on said first insulator layer;
   a P-plus layer and a P-well layer formed on a perimeter of said semiconductor substrate wherein said P-plus layer and said P-well layer create a path for a parasitic capacitance caused by water condensation to connect to at least one node of a sensing capacitor;
   a pair of contacts associated with a pair of capacitor plates formed on said second insulator layer, wherein said pair of capacitor plates are isolated from one another with a space formed therein; and
   a humidity sensitive dielectric layer formed on said second insulator layer and said pair of capacitor plates, wherein a relative permittivity of said humidity sensitive layer varies in accordance with a humidity such that a pair of series capacitance additionally varies in accordance with said humidity to thereby provide an increased accurate measurement of said humidity.

2. The apparatus of claim 1 further comprising a porous electrically conductive plate formed on said humidity sensitive dielectric layer, wherein said porous electrically conductive plate forms a common top plate with respect to said pair of capacitive plates.

3. The apparatus of claim 2 further comprising;
   a protective layer located on said porous electrically conductive plate, wherein said protective layer protects said common top plate and said humidity sensitive layer.

4. The apparatus of claim 1 wherein said first insulator layer comprises a silicon oxide.

5. The apparatus of claim 1 wherein said second insulator layer comprises a silicon nitride.

6. The apparatus of claim 1 wherein said first insulator layer comprises a silicon oxide and said second insulator layer comprises a silicon nitride.

7. The apparatus of claim 1 further comprising:
   a porous electrically conductive plate formed on said humidity sensitive dielectric layer, wherein said porous electrically conductive plate form a common top plate with respect to said pair of capacitive plates; and
   a protective layer located on said porous electrically conductive plate, wherein said protective layer protects said common top plate and said humidity sensitive layer.

8. The apparatus of claim 1 further comprising
   a porous electrically conductive plate formed on said humidity sensitive dielectric layer, wherein said porous electrically conductive plate form a common top plate with respect to said pair of capacitive plates; and
   a protective layer located on said porous electrically conductive plate, wherein said protective layer protects said common top plate and said humidity sensitive layer, wherein said first insulator layer comprises a silicon oxide and said second insulator layer comprises a silicon nitride.

9. The apparatus of claim 1 wherein said P-plus layer and said P-well layer are fabricated utilizing a standard silicon wafer processing technique.

10. An improved relative humidity sensor apparatus, comprising:
    a semiconductor substrate and a first insulator layer formed on said semiconductor substrate in association with a second insulator layer formed on said first insulator layer;
    a P-plus layer and a P-well layer formed on a perimeter of said semiconductor substrate wherein said P-plus layer and said P-well layer create a path for a parasitic capacitance caused by water condensation to connect to at least one node of a sensing capacitor;
    a pair of contacts associated with a pair of capacitor plates formed on said second insulator layer, wherein said pair of capacitor plates are isolated from one another with a space formed therein;
    a humidity sensitive dielectric layer formed on said second insulator layer and said pair of capacitor plates;
    a porous electrically conductive plate formed on said humidity sensitive dielectric layer, wherein said porous electrically conductive plate includes a common top plate with respect to said pair of capacitive plates; and
    a protective layer located on said porous electrically conductive plate, wherein said protective layer protects said common top plate and said humidity sensitive layer, wherein a relative permittivity of said humidity sensitive layer varies in accordance with a humidity such that a pair of series capacitance additionally varies in accordance with said humidity to thereby provide an increased accurate measurement of said humidity.

11. The apparatus of claim 10 wherein said first insulator layer comprises a silicon oxide.

12. The apparatus of claim 10 wherein said second insulator layer comprises a silicon nitride.

13. The apparatus of claim 10 wherein said first insulator layer comprises a silicon oxide and said second insulator layer comprises a silicon nitride.

14. A method of forming an improved relative humidity sensor apparatus, comprising:
    providing a semiconductor substrate and a first insulator layer formed on said semiconductor substrate in association with a second insulator layer formed on said first insulator layer;
    forming a P-plus layer and a P-well layer on a perimeter of said semiconductor substrate wherein said P-plus layer and said P-well layer create a path for a parasitic capacitance caused by water condensation to connect to at least one node of a sensing capacitor;
    associating a pair of contacts with a pair of capacitor plates formed on said second insulator layer, wherein said pair of capacitor plates are isolated from one another with a space formed therein; and
    forming a humidity sensitive dielectric layer on said second insulator layer and said pair of capacitor plates, wherein a relative permittivity of said humidity sensitive layer varies in accordance with a humidity such that a pair of series capacitance additionally varies in accordance with said humidity to thereby provide an increased accurate measurement of said humidity.

15. The method of claim 14 further comprising configuring a porous electrically conductive plate on said humidity sensitive dielectric layer, wherein said porous electrically conductive plate includes a common top plate with respect to said pair of capacitive plates.

16. The method of claim 14 further comprising locating a protective layer on said porous electrically conductive plate, wherein said protective layer protects said common top plate and said humidity sensitive dielectric layer.

17. The method of claim 14 wherein said first insulator layer comprises a silicon oxide.

18. The method of claim 14 wherein said second insulator layer comprises a silicon nitride.

19. The method of claim 14 wherein said first insulator layer comprises a silicon oxide and said second insulator layer comprises a silicon nitride.

20. The method of claim 14 further comprising fabricating said P-plus layer and said P-well layer utilizing a standard silicon wafer processing technique.

* * * * *